US008043297B2

(12) United States Patent
Grady, Jr. et al.

(10) Patent No.: US 8,043,297 B2
(45) Date of Patent: Oct. 25, 2011

(54) AIMING ARM FOR BONE PLATES

(75) Inventors: Mark P. Grady, Jr., West Chester, PA (US); Scott DiDomenico, Warrington, PA (US); Keith A. Mayo, Gig Harbor, WA (US); Jeff W. Mast, Reno, NV (US); Brett R. Bolhofner, St. Petersburg, FL (US)

(73) Assignee: Synthes USA, LLC, West Chester, PA (US)

( * ) Notice: Subject to any disclaimer, the term of this patent is extended or adjusted under 35 U.S.C. 154(b) by 1459 days.

(21) Appl. No.: 10/981,191

(22) Filed: Nov. 3, 2004

(65) Prior Publication Data

US 2006/0095044 A1 May 4, 2006

(51) Int. Cl.
*A61B 17/60* (2006.01)
*A61F 2/00* (2006.01)
(52) U.S. Cl. .......................................................... 606/98
(58) Field of Classification Search ............... 606/96–98, 606/103–104
See application file for complete search history.

(56) References Cited

U.S. PATENT DOCUMENTS

| 2,424,485 | A | * | 7/1947 | Miller | 408/115 B |
|---|---|---|---|---|---|
| 5,429,641 | A | * | 7/1995 | Gotfried | 606/67 |
| 5,669,915 | A | * | 9/1997 | Caspar et al. | 606/96 |
| 7,033,363 | B2 | * | 4/2006 | Powell | 606/96 |
| 7,357,804 | B2 | * | 4/2008 | Binder et al. | 606/96 |
| 2003/0083667 | A1 | | 5/2003 | Ralph et al. | |
| 2004/0030339 | A1 | | 2/2004 | Wack et al. | |
| 2005/0049594 | A1 | | 3/2005 | Wack et al. | |

FOREIGN PATENT DOCUMENTS

EP 0468192 1/1992

* cited by examiner

*Primary Examiner* — Anu Ramana
(74) *Attorney, Agent, or Firm* — Fay Kaplun & Marcin, LLP

(57) ABSTRACT

An aiming guide aligns a surgical tool with a hole in a bone plate. The aiming guide includes an arm portion having a longitudinal axis, top and bottom surfaces, and first and second ends. The aiming guide further includes a handle portion having upper and lower ends. The handle portion is, at its lower end, connected to the bone plate. The handle portion is, at its upper end, connected to the arm portion. Bores extend from the top surface to the lower surface of the arm portion. Each bore is configured and dimensioned to receive a tool guide in at least two different preset positions which locates the channel in at least two different hole positions. The bore includes two diametrically opposed slots extending along at least a portion of a length of the bore, the slots configured and dimensioned to mate with diametrically opposed knobs extending radially outward from a tool guide. The tool guide has a head and a sleeve portion, which has a centered channel. The sleeve portion and channel are eccentric with respect to the head portion. The tool guide is inserted in a first preset position in order to align a surgical tool with one portion of a two-portion bone plate hole, or in a second preset position rotated 180° from the first preset position, in order to align a surgical tool with the second portion of a two-portion bone plate hole.

44 Claims, 18 Drawing Sheets

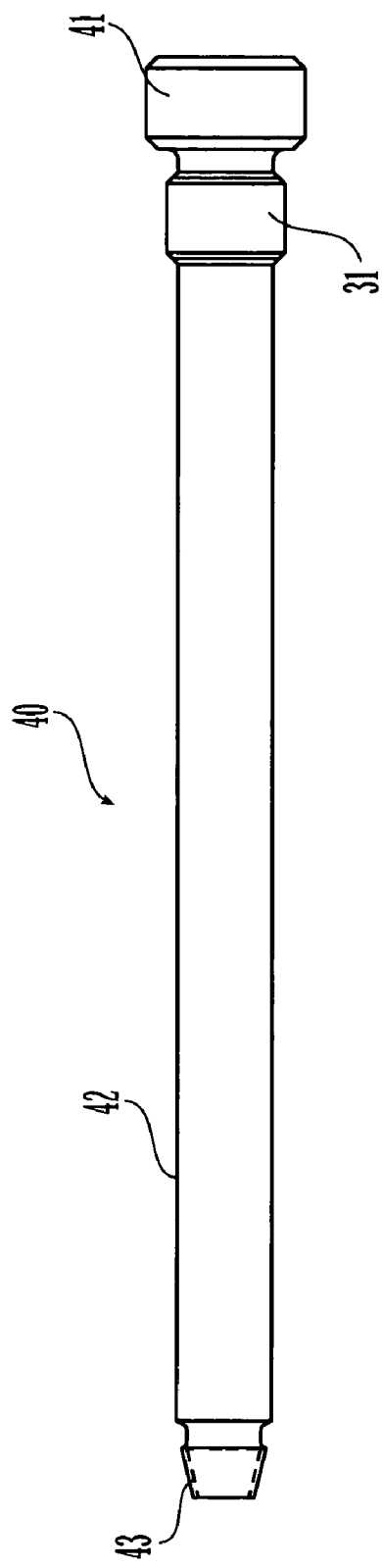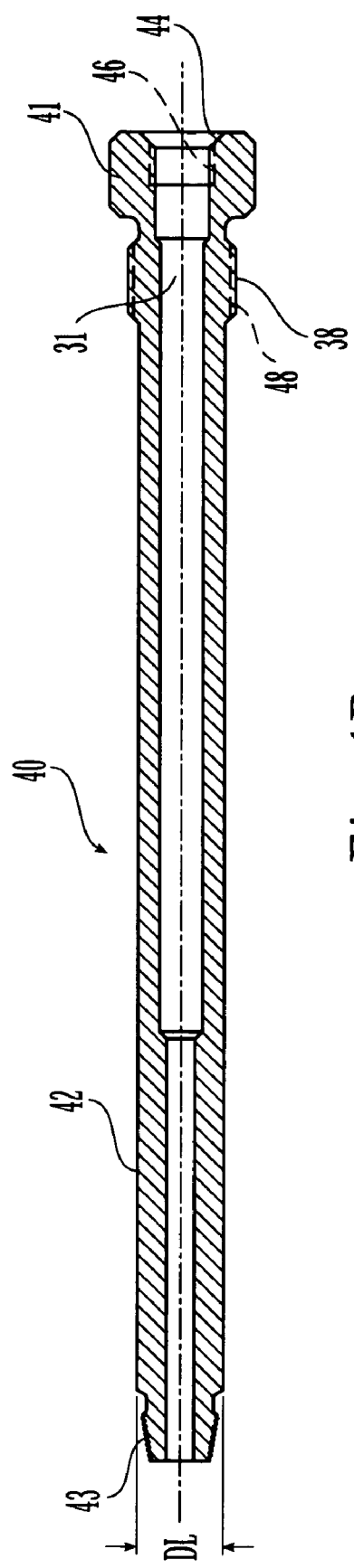

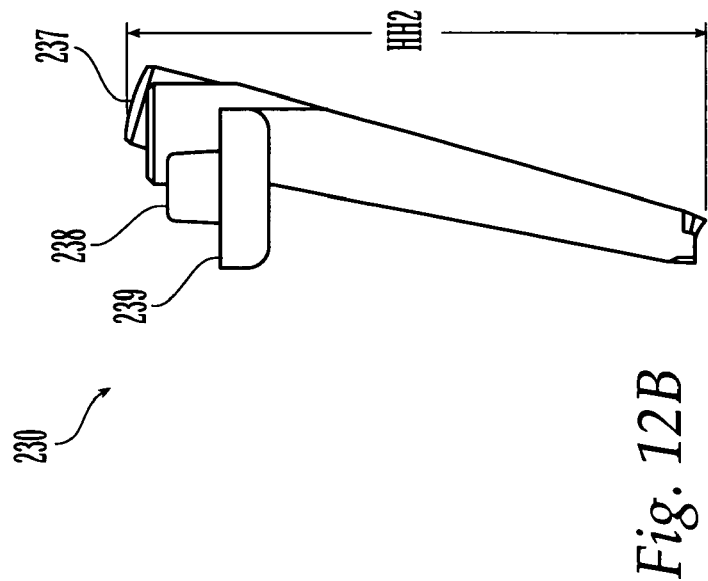
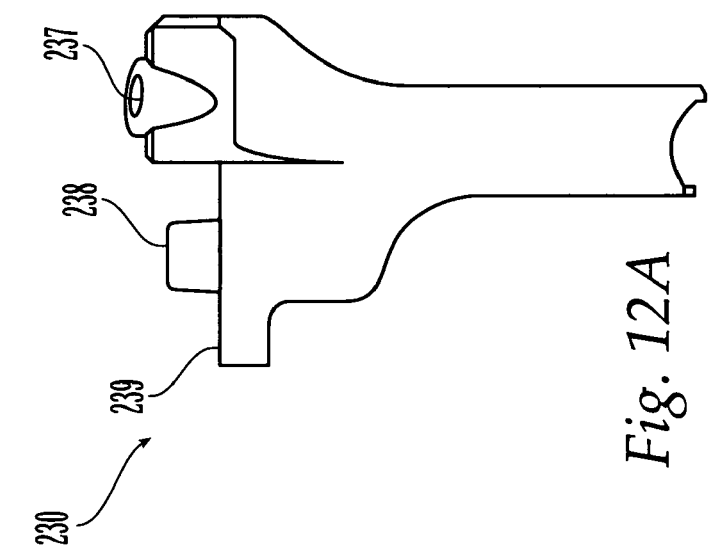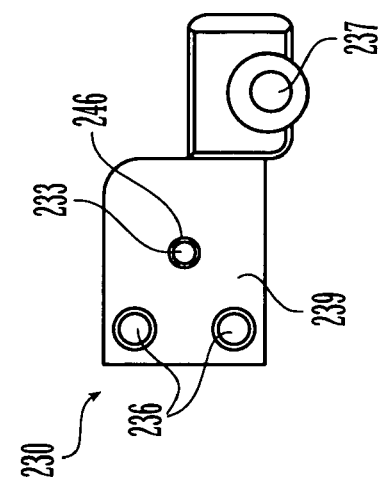
Fig. 12B
Fig. 12A
Fig. 12C

AIMING ARM FOR BONE PLATES

FIELD OF THE INVENTION

The present invention relates to an apparatus for aligning surgical tools (e.g., drill bit, trochar) with a hole in bone plate.

BACKGROUND OF THE INVENTION

Surgical devices which align tools (e.g., drill bits, trochars) to bone plate holes are known in the art. Many of these devices are not adjustable. Some of these known devices can be adjusted by the surgeon or operator to tailor it for use with a number of different bone plates which have varying hole placement arrangements or patterns. These adjustable devices, however, require the surgeon or operator to manually adjust the guide to suit the particular plate being used. Making these adjustments can be tedious and often requires trial and error. Furthermore, even after a surgeon adjusts one of these devices, the alignment between the guide and a respective plate hole may be imprecise. These problems become even more salient when the device being used is intended to align a tool (e.g., a drill bit) with so-called bone plate "combination holes." Indeed, it appears that no existing alignment device is designed for, or even particularly compatible with, a plate that has combination holes. A "combination hole," as used here, means any kind of hole in which there are multiple "hole positions" any one of which a surgeon can drill or operate through. For an example, see the combination holes disclosed in U.S. Pat. No. 6,669,701 and the combination holes disclosed in U.S. Pat. No. 6,719,759, the specifications of which are hereby incorporated by reference.

There thus exists a need for a device that will align a surgical tool (e.g., drill bit) with a bone plate hole or that can be "adjusted" or aligned with a bone plate hole or a portion of a bone plate hole with minimal effort and maximum precision. This need is especially evident when a bone plate having combination holes is used. The present invention addresses this problem and others by providing an aiming arm which has aligning bores, whose arrangement matches or corresponds to the arrangement of holes of a particular bone plate type. When adjustment is needed, for example when a bone plate that has combination holes is being used, the present invention may provide an aiming arm that has guide bores, each guide bore having multiple (i.e., at least 2) preset positions in which to introduce or position a guide sleeve, each position providing for alignment with a particular, different hole portion. Because the positions are preset, maneuvering each guide sleeve to the desired position is very easy and takes a very short amount of time.

SUMMARY OF THE INVENTION

The aiming guide system of the present invention provides alignment between a surgical tool (e.g., a drill bit, a trochar) and holes or hole portions in a bone plate.

The aiming guide system may be used with a bone plate having virtually any hole distribution arrangement and virtually any hole configuration. In a preferred embodiment, the aiming guide system is used with a plate having "combination holes." A combination hole is any kind of hole in which there are multiple "hole positions" any one of which a surgeon can penetrate or access. One example of a combination hole is an elongated hole extending from an upper surface of a bone plate to a lower surface of a bone plate, and which has a threaded portion and a non-threaded portion. The threaded portion may extend over a range of greater than half of the hole's circumference. The threaded portion of the hole may be dimensioned and configured to engage a threaded head of a bone screw, and fix the bone screw at a predetermined angle with respect to the bone plate. The same type of screw or other types of screws, including screws not having threaded heads, may pass through the non-threaded portion of a combination hole at any one of a number of angles.

The aiming guide system may have an aiming arm. In a first preferred embodiment, the arm extends substantially parallel to the bone plate in its lengthwise direction and has multiple bores. In a second preferred embodiment, the arm curves sideways, away from the bone plate. There may be any number of bores in the aiming arm. The arrangement/pattern of the bores preferably matches or corresponds to the arrangement/pattern of the holes in the bone plate. Each bore is preferably aligned with the center of a corresponding bone plate hole (which may be in between the respective centers of each hole portion). In the second preferred embodiment in which the arm curves away from the bone plate, the bores may be oriented at a non-perpendicular angle with respect to the plane defined by the top surface of the arm.

In a preferred embodiment, a tool guide may be positioned to run substantially straight between a bore of the aiming arm and a corresponding bone plate hole. In a preferred embodiment, the guide has a head and a sleeve. A channel may extend through the head and sleeve. The channel may be centered with respect to the sleeve. The channel and sleeve may be eccentric with respect to the head of the guide and the bore of the arm (i.e., the channel and sleeve may not be positioned at the geometric center of the head and bore). This eccentricity serves, as described below, to align the guide sleeve with any one of multiple positions within a given combination hole.

In a preferred embodiment, the tool guides have, at their heads, two radially-extending, diametrically-opposed knobs. The knobs may mate with two corresponding diametrically opposed slots formed in the inner surface of each of the bores of aiming arm. Thus, when positioned in the slots, the knobs prevent a tool guide from rotational movement relative to the bore and arm. The lock neutral guide may be placed within the bore in either of two possible positions. In one position, the eccentric channel (and sleeve) is offset from center in one direction and is therefore aligned with one side of a combination hole. In the other position, 180 degrees rotated from the first position, the eccentric channel (and sleeve) is offset from center in the opposite direction and is therefore aligned with the other side of the combination hole. To accomplish this, the knobs of the tool guide and the slots of the bores may be dimensioned and configured such that the eccentricity of the sleeve and channel is offset from the center in a direction corresponding with the direction of the array of hole positions within a given plate hole. The surgeon thus has the option to align the sleeve, and hence the surgical tool being used, with either of the hole portions of a combination hole.

In a preferred embodiment, a handle connects the aiming arm to the bone plate. The handle, at its lower end, may be secured to the bone plate. A locking bolt may penetrate a substantially vertical chamber in the handle and may secure the handle to the bone plate by being threaded into a bone plate hole. The handle, at its upper end, may be secured to the aiming arm. In a preferred embodiment, the handle is secured to the aiming arm by a coupling bolt. The coupling bolt may have a head and a shaft. The shaft may pass through a corresponding hole in the aiming arm and mate with a hole located at the top surface of the head of the interlocking bolt or at an upper surface of the handle

BRIEF DESCRIPTION OF THE DRAWINGS

These figures represent preferred embodiments of the aiming guide system. Those skilled in the art will recognize that numerous variations and modifications may be made without departing from the scope of the present invention. Accordingly, it should be understood that these figures are not intended as limitations on the scope of the invention, which is defined only by the claims.

FIG. 4A is a side view of the interlocking bolt.

FIG. 4B is a cross-sectional view of the interlocking bolt of FIG. 4A.

FIG. 12A is a side view of the handle of FIG. 11.

FIG. 12B is a side view of the handle of FIG. 11, rotated 90° from the view of FIG. 12A.

FIG. 12C is a is a top view of the handle of FIG. 2.

DESCRIPTION OF THE PREFERRED EMBODIMENTS

The aiming guide system is described below with reference to the illustrated embodiments. Those skilled in the art will recognize that numerous variations and modifications may be made without departing from the scope of the present invention. Accordingly, it should be understood that the embodiments of the invention described above are not intended as limitations on the scope of the invention, which is defined only by the claims.

Figure 1A:
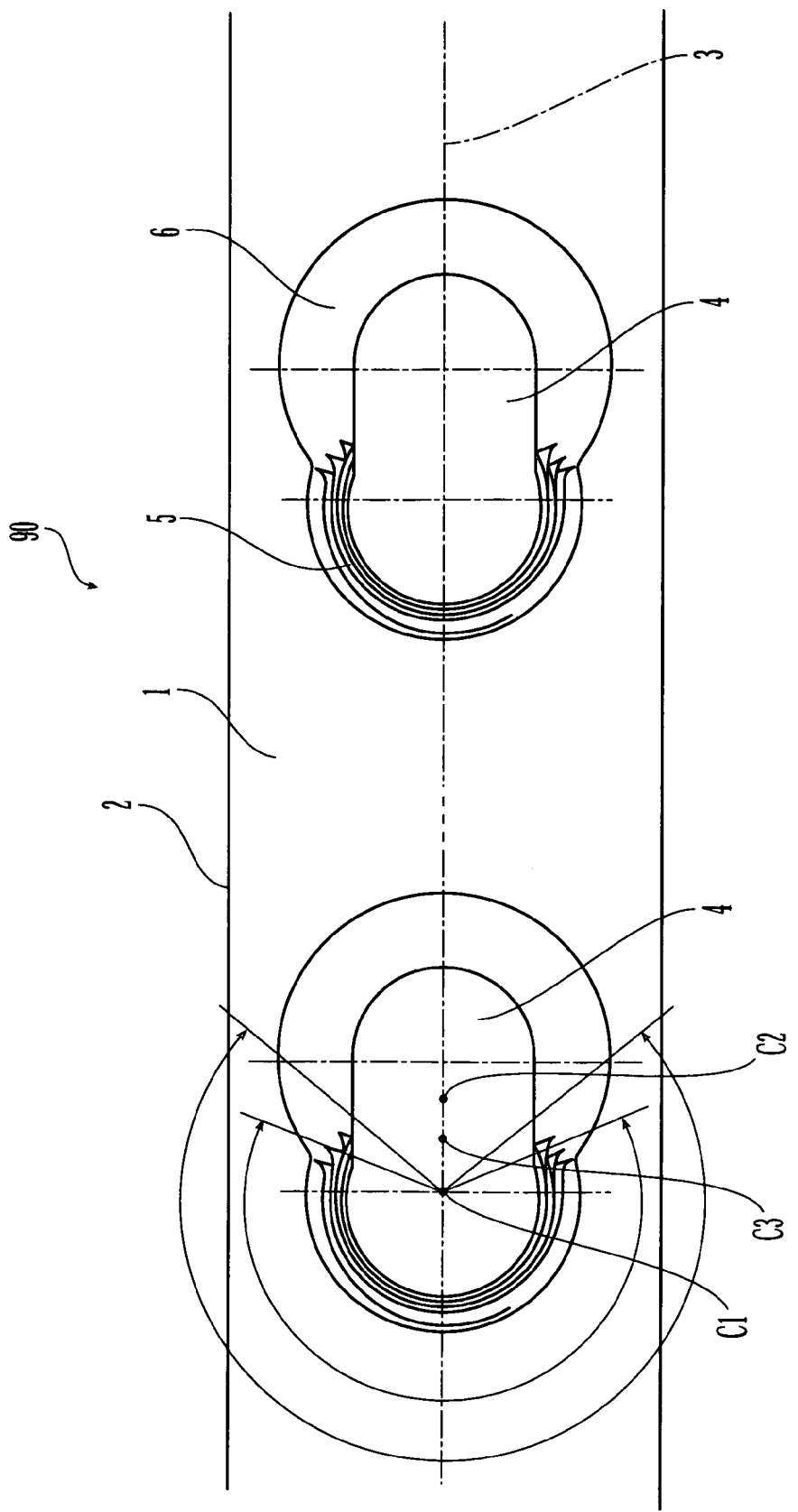
FIG. 1A is a plan view of a segment of a bone plate having combination holes.

FIG. 1A illustrates one example of a section of a bone plate 90 having one illustrative embodiment of holes 4 with which the aiming guide system is intended to be used. FIG. 1A illustrates a bone plate 90 which includes an upper surface 1, a bone contacting or lower surface 2 (not shown), and a plurality of combination holes 4 extending through the upper surface 1 and lower surface 2. The holes 4 may be elongated (e.g., in a direction substantially aligned with a longitudinal axis of the plate) and may include a threaded portion 5 and a non-threaded portion 6. The threaded portion 5 may extend over a range of greater than about 180° with respect to a center point C1 of a first circular portion P1 along which the threaded portion lies (discussed below). The threaded portion 5 of the hole 4 may be dimensioned and configured to engage a threaded head of a bone screw, and fix the bone screw at a predetermined angle with respect to the bone plate. Preferably, the threaded portion 5 extends through the full thickness of the bone plate, i.e., from the upper surface 1 to the lower surface 2, thus maximizing the stability of the bone screw to bone plate interface. The same type of screw, or other types of screws, including screws not having threaded heads, may pass through the non-threaded portion 6 of a combination hole 4. The specifications of U.S. Pat. No. 6,669,701 and of U.S. Pat. No. 6,719,759 disclose combination holes and are hereby incorporated by reference.

Figure 1B:
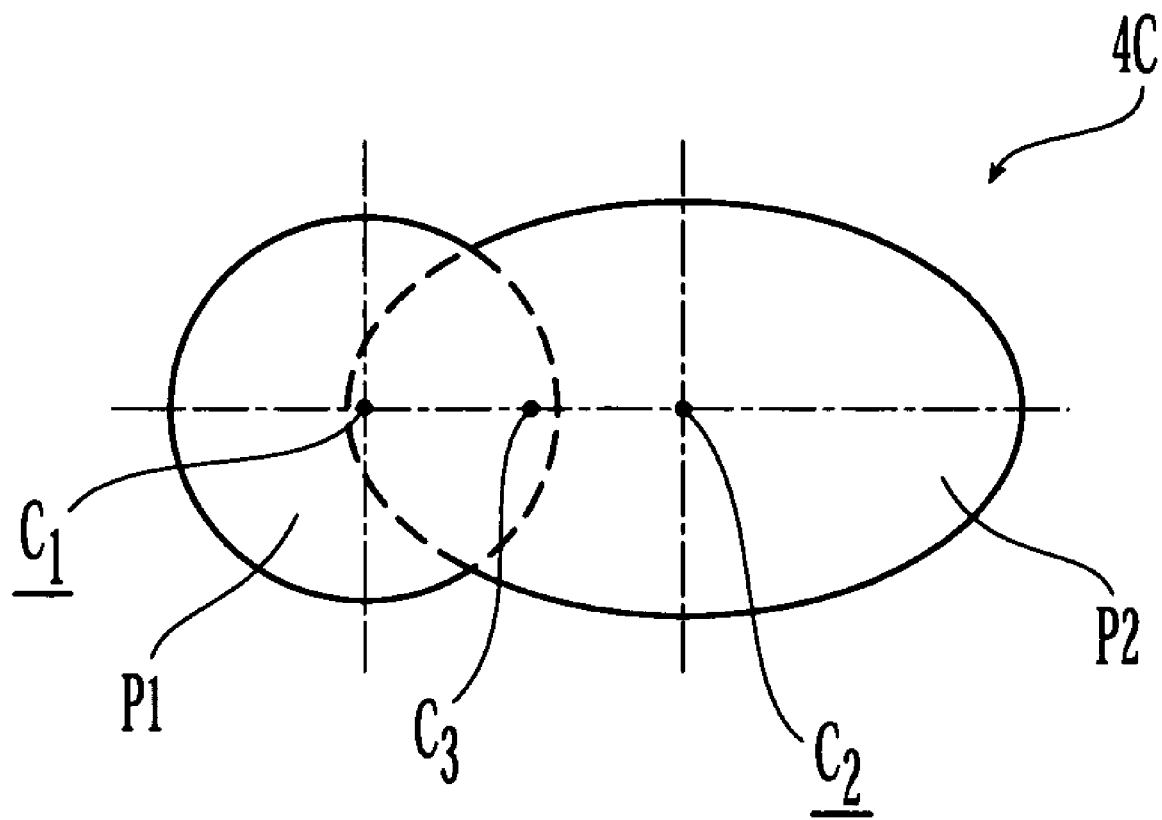
FIG. 1B is a schematic representation of a combination hole of the bone plate of FIG. 1A.

FIG. 1B is a schematic representation of the combination hole of FIG. 1A. This combination hole may have a first circular portion P1 (along which the threaded portion 5 may lie) and a second elongated portion P2 (along which the non-threaded portion 6 may lie). The first circular portion P1 and the second elongated portion P2 overlap one another and are thus in communication with one another. The first circular portion P1 defines a first center point C1. The second elongated portion P2 defines a second center point C2. In between these two points is a central point C3.

Figure 2:
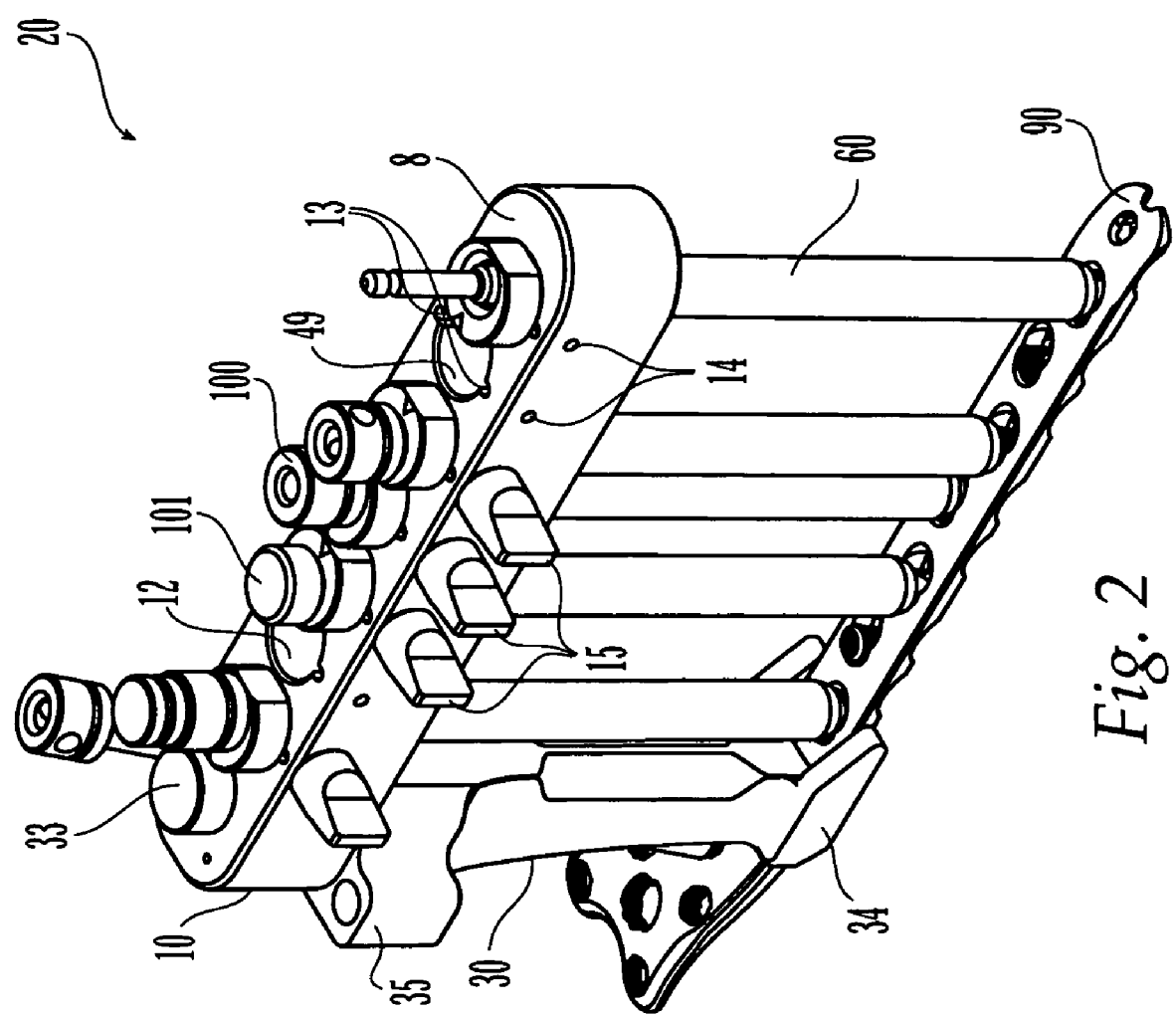
FIG. 2 is a perspective view of the assembled components of a first embodiment of the aiming guide system of the present invention.
Figure 14A:
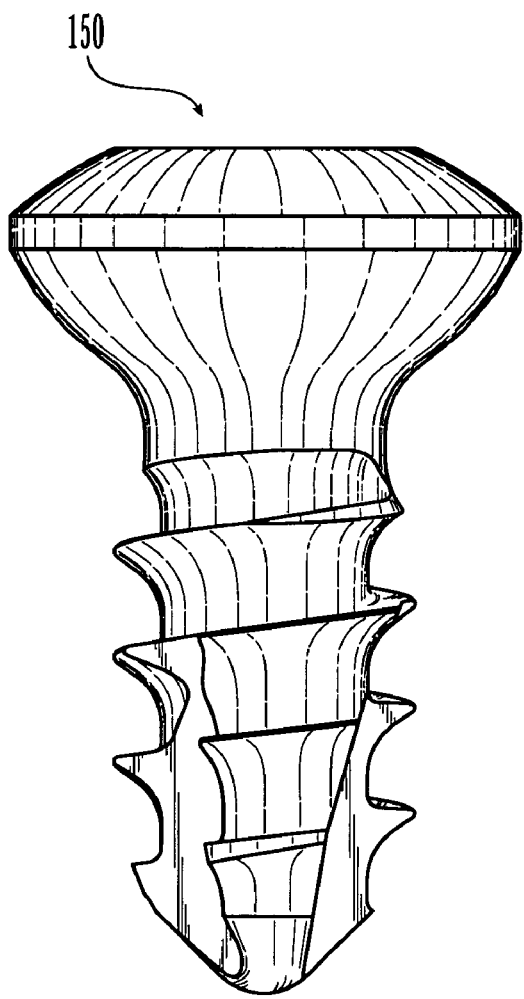
FIGS. 14A and 14B are side views of two examples of a bone anchor that may be used with the aiming guide system.
Figure 14B:
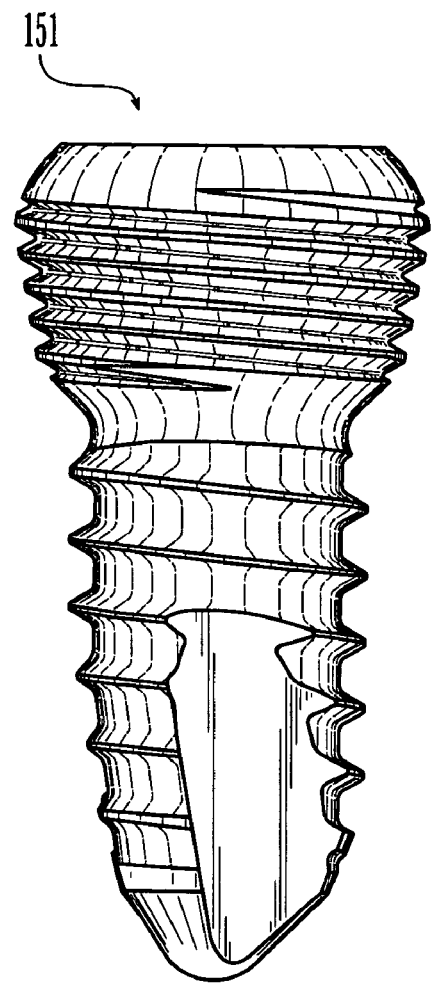

Reference is now made to FIG. 2, which is a perspective view of the assembled components of a first preferred embodiment of the aiming guide system 20. The aiming guide system 20 provides alignment between a surgical tool (e.g., a drill bit 100, a trochar 101) and holes or hole portions in a bone plate. By use of the aiming guide system, a bone anchor (e.g., bone screws 150 and 151 shown in FIGS. 14A and 14B, a pin, a tack) can be properly aligned with the holes in the bone plate.

Though the aiming guide systems 20 and 220 are described in the context of certain bone plates with certain hole arrangements and hole configurations, it should be noted that the aiming device may be utilized with any bone plate with virtually any hole distribution arrangement and virtually any hole configuration.

In this first preferred embodiment, the aiming guide system 20 includes a handle 30. The handle 30, at its lower end 34, may be attached to a bone plate 90. The handle 30, at its upper end 35, may be attached to, or may be integral with, an aiming arm 10. The aiming arm 10 may extend substantially parallel to the bone plate 90 in the lengthwise direction and may have multiple bores 12. There may be any number of bores 12 in aiming arm 10. The arrangement/pattern of the bores 12 preferably matches the arrangement/pattern of the holes in the bone plate 90. FIG. 8C is a plan view of the top surface of aiming arm 10. The bores 12 may be staggered to match a bone plate with a corresponding arrangement of staggered holes. Each bore 12 is preferably aligned with the central point (C3 in FIGS. 1A and 1B) of a corresponding bone plate hole.

The aiming arm 10 is substantially straight along its longitudinal axis and the bores 12 may be substantially perpendicular to the top surface 8 of the aiming arm 10. The top surface 8 of the aiming arm 10 is also substantially flat and planar. As discussed more fully below in connection with the description of another embodiment, the bores 12 may extend through the arm 10 at a non-perpendicular angle with respect to the top surface 8 of arm 10 and may be angled in one, two, or three planes. In addition, as discussed more fully below, the top surface 8 of the arm 10 may be curved and/or twisted along its longitudinal axis, curved and/or twisted along its width, or curved in both directions. The aiming arm 10 also may bowed instead of flat and planar.

A tool guide, for example lock neutral guide 60, may be positioned in a bore 12 of the aiming arm and may extend to a corresponding bone plate hole 4. Thumb screws 15 may be inserted (e.g., threaded) into side holes 14 in the aiming arm 10 in order to retain the guides 60 in the bores 12. The guide 60 may be inserted into the bore 12 in one of at least two different preset positions in order to align the guide 60 with a particular hole portion of a bone plate hole 4. (The details of which are illustrated in FIGS. 3, 8A-8C and 9A-9C and are discussed more fully below.) A tool (e.g., a drill bit, a trochar) may be received by the guide 60 and thereby aligned with a targeted hole portion of a given hole 4.

Figure 3:
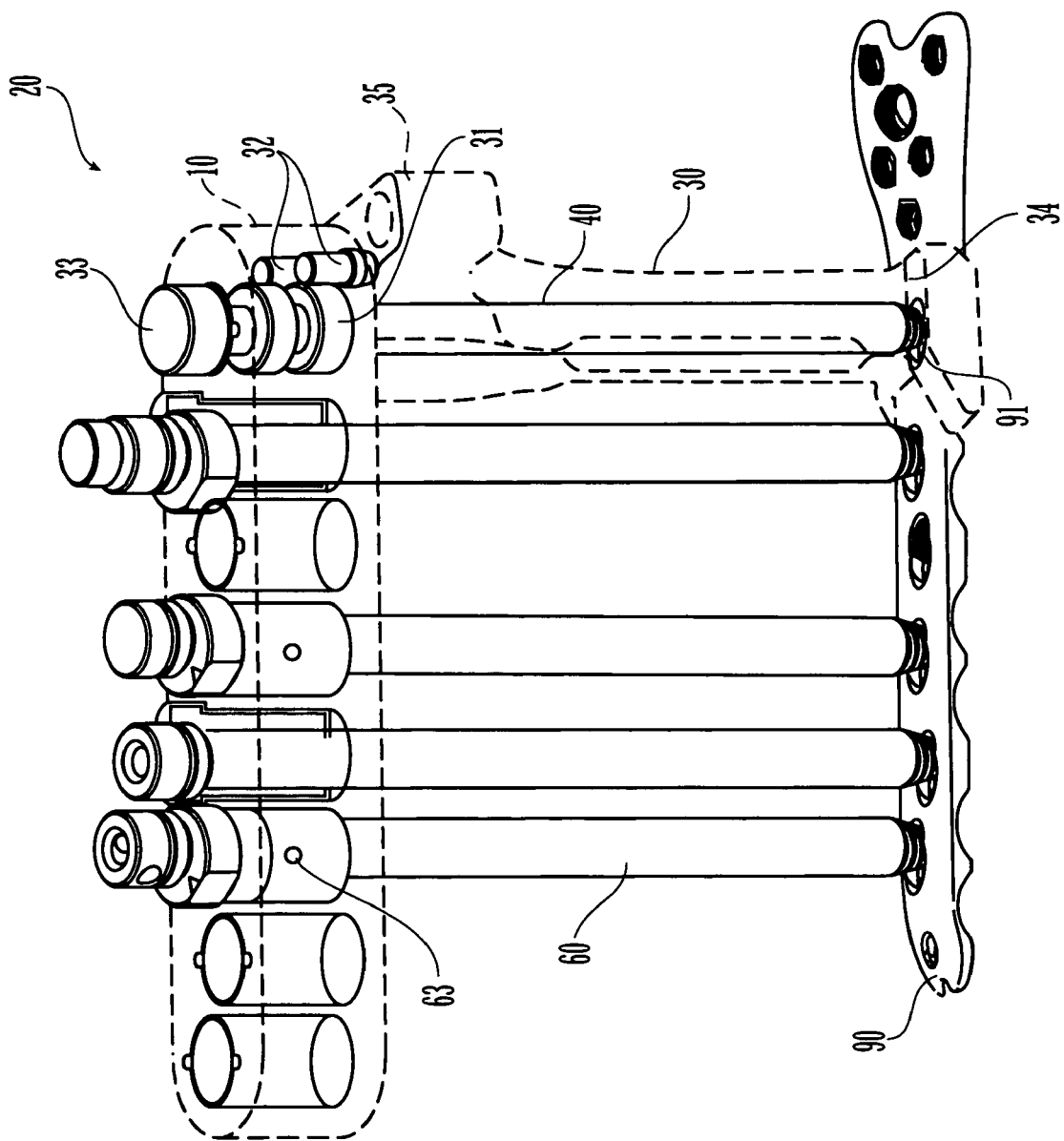
FIG. 3 is a side view of the aiming guide system of FIG. 2.

Reference is now made to FIG. 3, which is a side view of the assembled components of the first preferred embodiment of the present invention. The handle 30 may, at its lower end 34, be attached to the bone plate 90 in any number of ways. In a preferred embodiment, the handle 30 is attached to the bone plate 90 by an interlocking bolt 40, which threads into a specific reference-point hole 91 in the bone plate 90. As shown in FIG. 4A, the interlocking bolt 40 may have a head 41, a shaft 42, and an externally-threaded end 43.

Figure 5A:
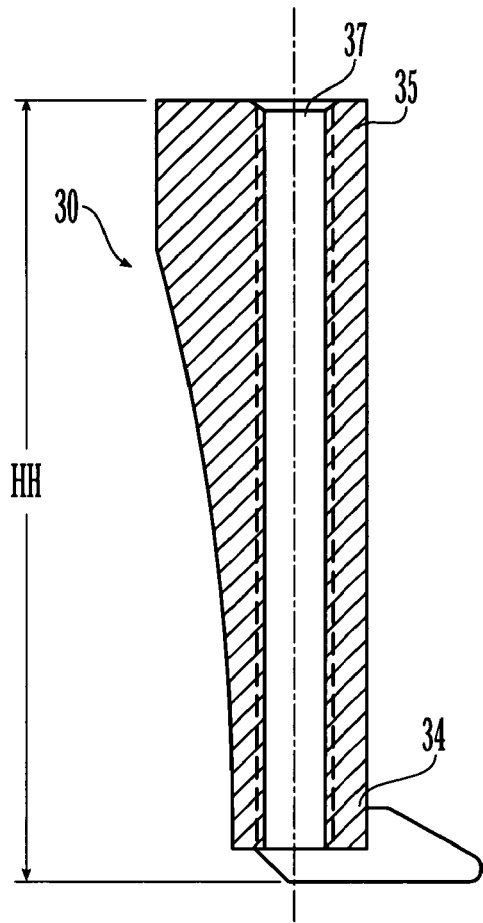
FIG. 5A is a cross-sectional view of the handle of FIG. 2.
Figure 5B:
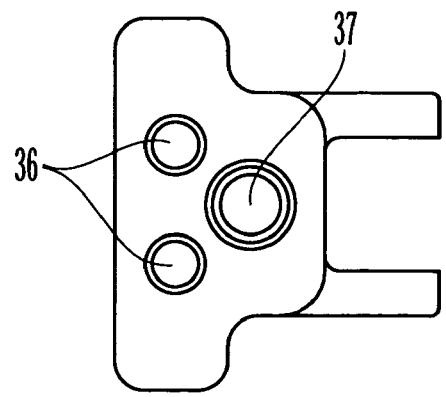
FIG. 5B is a top view of the handle of FIG. 2.

In a preferred embodiment, the lower end 34 of handle 30 is wider than, and straddles, the bone plate 90. As shown in FIGS. 5A and 5B, the handle 30 may have a longitudinal bore or chamber 37 for insertion of interlocking bolt 40. As shown in FIG. 5A, the chamber 37 may extend from the upper surface to the lower surface of handle 30. After the handle 30 is positioned on the bone plate 90, the interlocking bolt 40, may be dropped or rotated through the chamber 37 and threaded into hole 91 in the bone plate 90, while the handle 30 is kept stationary. For ease of alignment between the interlocking bolt 40 and the reference hole 91 during insertion of the interlocking bolt 40, interlocking bolt 40 may be cannulated to allow for the insertion of a guide wire through the interlocking bolt 40 and into hole 91 in the bone plate 90.

Figure 6A:
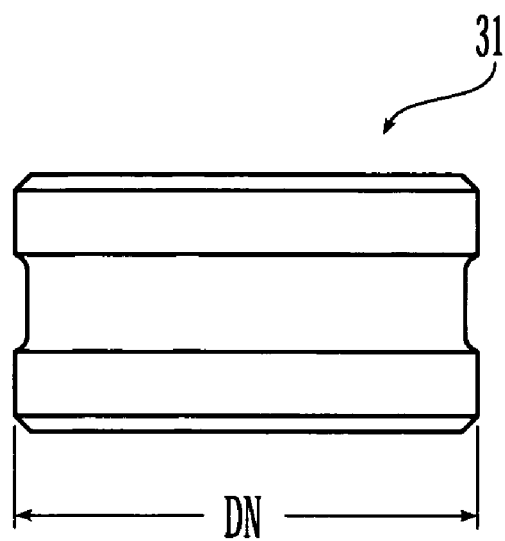
FIG. 6A is a side view of the locking nut.
Figure 6B:
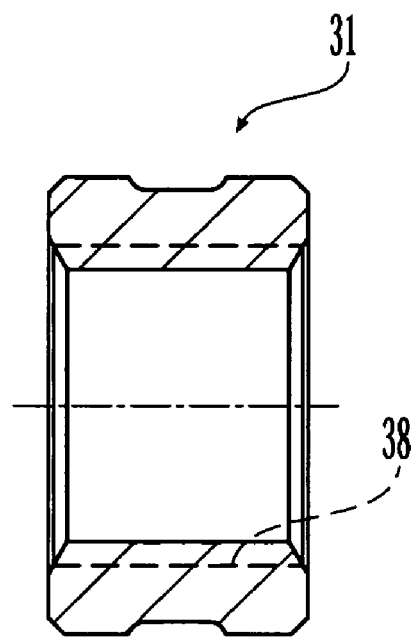
FIG. 6B is a cross-sectional view of the locking nut of FIG. 6A.

Before inserting the interlocking bolt 40 through the chamber 37 of the handle 30, a locking nut 31 (shown in FIG. 6A) may be positioned on the shaft 42 of the interlocking bolt 40 and positioned to abut the head 41 of the interlocking bolt 40. As shown in FIGS. 6B and 4B, the locking nut 31 may have internal threads 38 to mate with an externally threaded portion 48 on the interlocking bolt 40. After the interlocking bolt 40 has been inserted through the chamber 37 of the handle and threaded into the hole 91 of the bone plate, the locking nut 31 may be rotated to take up any slack in the connection between the handle 30 and the bone plate 90. As shown in FIG. 6A, the locking nut 31 may knurled to aid the operator in gripping the nut 31 when rotating it.

The nut 31 preferably has a diameter DN of about 1.0 cm to 1.8 cm. The interlocking bolt 40 preferably has a length LI of about 13 cm to 14 cm and a primary diameter DI of about 0.7 cm to about 0.9 cm. The chamber 37 may have a diameter suitable to accommodate the interlocking bolt 40.

Handle 30, at its upper end 35, may be integral with, or attachable to, the aiming arm 10. The aiming arm 10 may be aligned with the handle 30 in any number of ways as those skilled in the art will appreciate. In a preferred embodiment, pins 32 serve to align the handle 30 with the aiming arm 10. In one embodiment, the pins may be integral with the handle 30 and mate with corresponding holes 17 in the arm 10, or vice versa. In another embodiment, unattached pins 32 may mate with corresponding holes 36 and 17 in both the handle 30 and arm 10, respectively. (See FIG. 8A.) Pin holes 36 in the top surface of handle 30 are shown in FIG. 5B. Pin holes 17 in the bottom surface of aiming arm 10 are shown in FIG. 8B.

Figure 7:
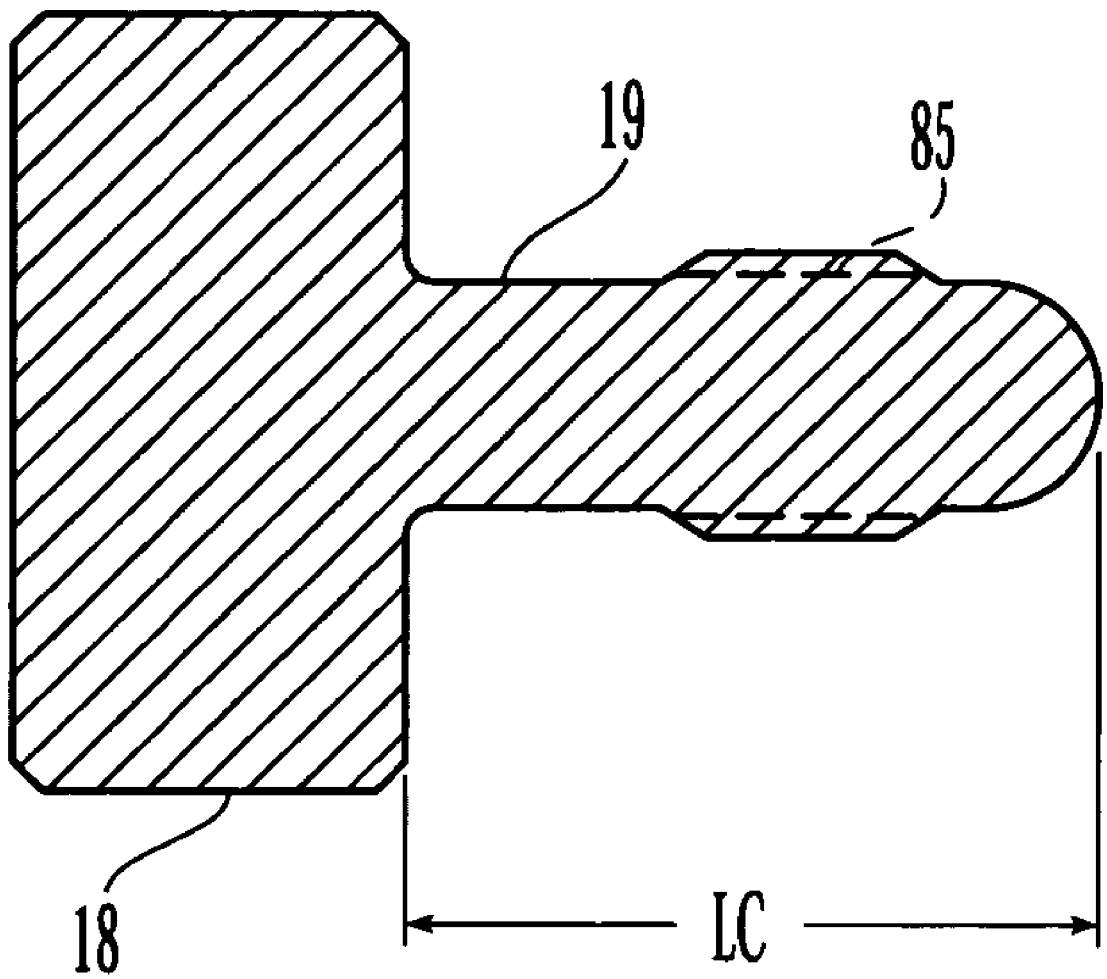
FIG. 7 is a cross-sectional view of the coupling bolt.

In a preferred embodiment, the handle 30 is removably attachable to the aiming arm 10. The handle 30 may be secured to the aiming arm 10 in any number of ways. One end of the aiming arm may be positioned over the top surface of the handle. There may be a space 87 (shown in FIG. 8B) in the bottom surface of aiming arm 10 to provide clearance for the head 41 of the interlocking bolt 40. In a preferred embodiment, the handle 30 is secured to the aiming arm 10 by a coupling bolt 33. As shown in FIG. 7, coupling bolt 33 may have a head 18 and a shaft 19. The shaft 19 may pass through a corresponding hole 16 (shown in FIG. 8B) in the aiming arm 10 and mate with a hole 44 located at the top surface of the head 41 of the interlocking bolt 40. Shaft 19 may have external threads 85 (shown in FIG. 7) to mate with corresponding internal threads 86 (identified in FIG. 8B) of the hole 16 of aiming arm 10 and to mate with corresponding internal threads 46 (shown in FIG. 4B) on the inner surface of hole 44 of the interlocking bolt 40.

Shaft 19 preferably has a length LC of about 1.1 cm to 1.7 cm and a diameter DC of about 0.4 cm to 0.6 cm. Handle 30 preferably has a height HH of about 10 cm to 14 cm.

Figure 8A:
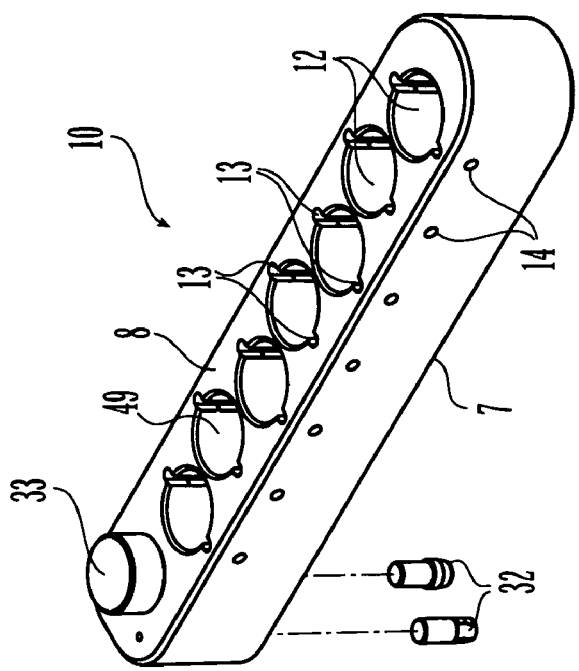
FIG. 8A is a perspective view of the aiming arm of FIG. 2.
Figure 8B:
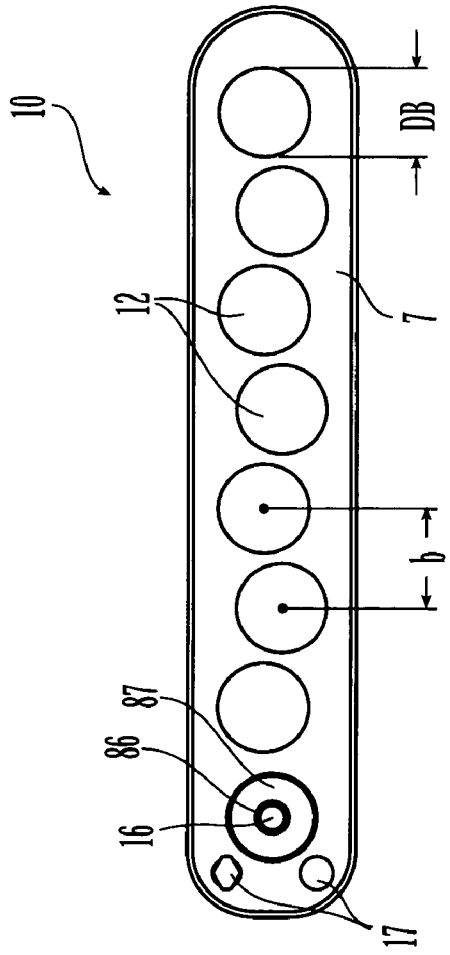
FIG. 8B is a bottom view of the aiming arm of FIG. 2.
Figure 8C:
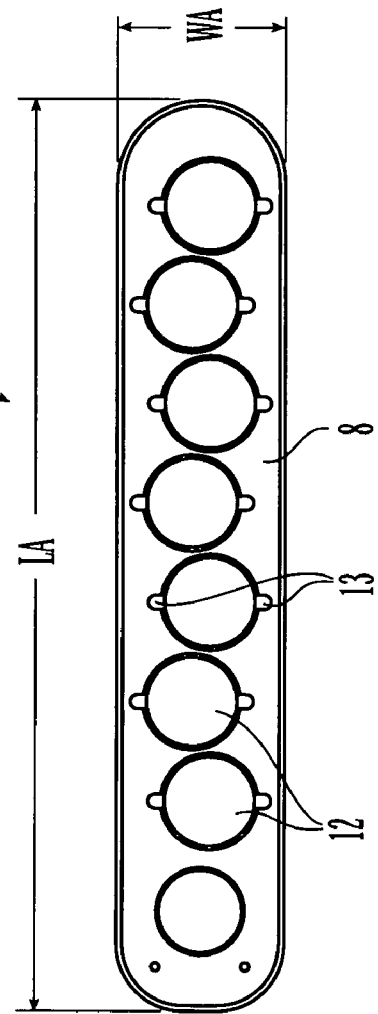
FIG. 8C is a top view of the aiming arm of FIG. 2.

FIGS. 8A (a perspective view of the aiming arm 10) and 8C (a top view of the aiming arm 10) illustrate bores 12, each having two diametrically opposed slots 13 formed in their inner surfaces 49. Slots 13 preferably do not extend from the top surface 8 to the bottom surface 7 of the aiming arm 10. Reference is made to FIG. 8B, which is a bottom view of the arm 10. In one embodiment in which the arm 10 has seven bores 12, the arm 10 preferably has a length LA of about 14 cm to about 19 cm and a width WA of about 2.5 cm to about 3.5 cm. Bore 12 preferably has a diameter DB of about 1.3 cm to about 1.9 cm. The distance b between adjacent bore 12 centers is preferably about 1.5 cm to about 2.1 cm. Depending upon the size of the bone plate and the arrangement of the bone plate holes, the length LA, width WA, distance b between adjacent bore holes, and the orientation of the bores 12 can be varied.

Figure 9C:
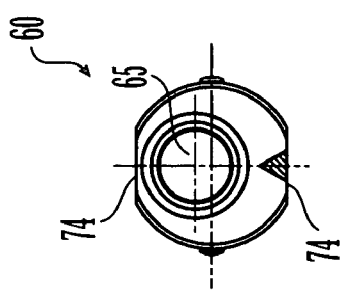
FIG. 9C is a plan view of the lock neutral guide of FIG. 9A.
Figure 9A:
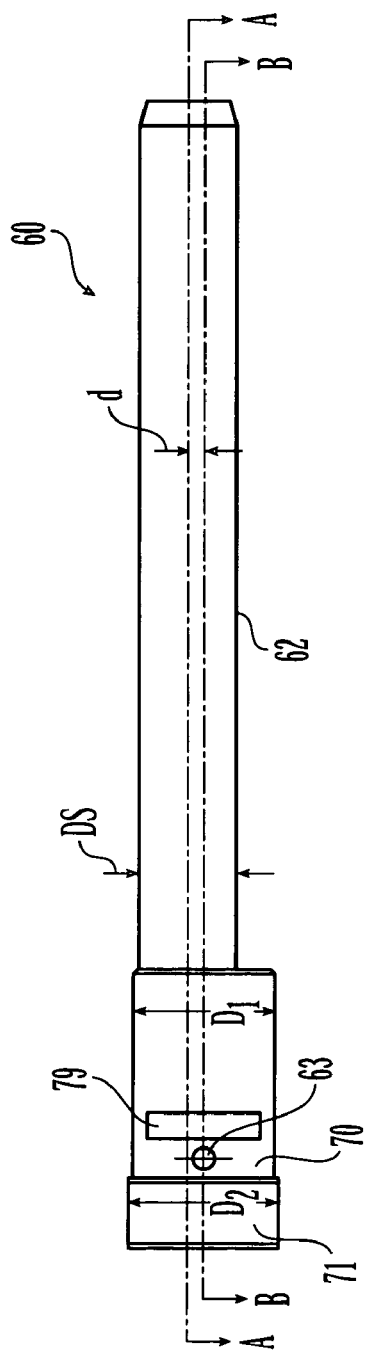
FIG. 9A is a side view of the lock neutral guide.
Figure 9B:
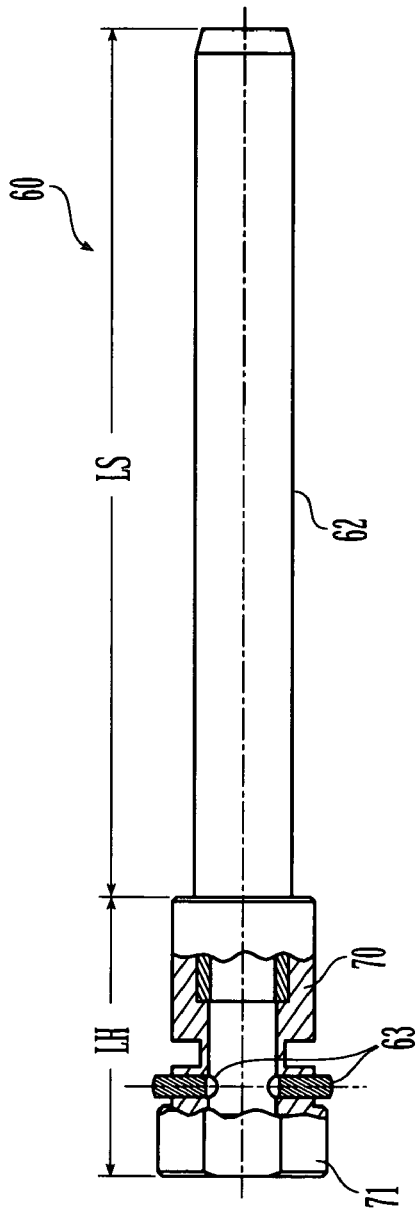
FIG. 9B is a side view, and partial cross-sectional, of the lock neutral guide of FIG. 9A, rotated 90 degrees.

As shown in FIGS. 9A and 9B, the lock neutral guide 60 may have a head 61 and a sleeve 62. A channel 65 may extend through the head 61 and sleeve 62. The channel 65 and sleeve 62 may be eccentric with respect to the head 61 and bore 12 (i.e., the channel and sleeve may not be positioned at the geometric center of the head 61 and bore 12). As shown in FIG. 9A, the central longitudinal axis B-B of the sleeve 62 may be offset from the central longitudinal axis A-A of the head 61. In a preferred embodiment, the distance d between axis A-A and axis B-B is preferably about 0.16 cm to about 0.20 cm. It will be appreciated that this eccentricity will serve to align the guide sleeve 62 with different portions of a combination hole (e.g., combination hole 4).

The heads 61 of the lock neutral guides 60 may have a first portion 70 with diameter D1 and a second portion 71 with diameter D2, the diameter D2 being greater than the diameter D1. The diameter D2 may also be greater than the Diameter D3 (shown in FIG. 9A) of the bore. Diameter D1 may be slightly smaller than D3 such that there is a slip fit between the first portion 70 of head 61 of guide 60 and the bore 12. The outer surface of the first portion 70 of guide 60 may contact the inner surface of the bore 12, but the "fit" between the two may be sufficiently loose to allow for manual movement of the guide 60 with respect to the bore 12. And when, as in this embodiment, diameter D2 of the second portion 71 is greater than diameter D3 of the bore, the second portion 71 will not fit within the bore 12 and instead will, at the appropriate point, stop the advancement of the guide 60 through the bore 12. Diameter D1 is preferably about 1.3 cm to about 1.8 cm. Diameter D2 is preferably about 1.7 cm to about 2.1 cm. Diameter D3 is preferably about 1.3 cm to about 1.9 cm.

In a preferred embodiment, as shown in FIG. 9B, the lock neutral guides 60 may have, at the circumferential outer surface of their heads 61, two radially-extending, diametrically-opposed knobs 63. Knobs 63 may mate with the two corresponding diametrically opposed slots 13 (shown in FIG. 8A) formed in the inner surface of the bores 12 of aiming arm 10. Thus, when positioned in slots 13, the knobs 63 prevent a lock neutral guide 60 from rotational movement relative to the bore 12 and arm 10. Lock neutral guide 60, in the embodiment of FIGS. 2 and 11, may be positioned within the bore 12 in either of two possible predetermined positions. In one position, the eccentric channel 65 and sleeve 62 is offset in one direction and is therefore aligned with one side of the combination hole. In the other position, 180 degrees rotated from the first position, the eccentric channel 65 (and sleeve 62) is offset in the opposite direction and is therefore aligned with the other side of the combination hole. To accomplish this, the knobs 63 of the tool guide and the slots 13 of the bores 12 may be dimensioned and configured such that the eccentricity of the sleeve 62 and channel 65 is offset from the center (of the bore 3 and head 61) in a direction and distance corresponding to the dimensions of the given plate hole. The surgeon thus has the option to align the sleeve 62, and hence the surgical tool, with either of the hole portions of a combination hole.

Shaft 62 of guide 60 preferably has a length LS of about 11 cm to about 12 cm and a diameter DS of about 0.7 cm to about 1.1 cm. Head 61 preferably has a length LH of about 3.0 cm to about 3.5 cm. Knobs 63 extend radially beyond the outer circumference of the head 61 preferably by about 0.20 cm to about 0.22 cm.

In one embodiment, the heads 62 of the lock neutral guides 60 may be generally circular. In a preferred embodiment, as shown in FIG. 9C, the second portion 71 of the head 62 may be generally circular, but have two segments of the circumference interrupted by two flat portions 74. Second portion 71 of head 62 may therefore be wide enough to prevent over-insertion of the guide 60 into the bore 12, but narrow enough in the direction facing other bores 12 to prevent heads 62 of guides 60 placed in closely adjacent bores from obstructing each other.

Any configuration or relationship between the lock neutral guide 60 and the bore 12 may be established and used to limit the guide 60 to preset positions within a bore 12 and to prevent relative rotational movement. For example, the mating arrangement could be reversed: the knobs could extend radially inward from the bore 12 and mate with slots formed on the outside of the guide 60. Also for example, instead of knobs 63, the guide 60 could have more sizeable (e.g. wider and longer) radially extending protrusions, to mate with corresponding recesses on the internal surface of the bore 12. In addition, the circumferential shape of head 62 and bores 12 could be keys so as to limit the position of the sleeve within the bore to one, two, or more predetermined positions so that the channel 65 will align with different areas of the bone plate hole depending upon the position of the head 62 with respect to the bore 12.

It will be appreciated that the eccentric channel 65 and sleeve 62 may be used with aiming arms having properties, features, and a configuration that are different from the aforedescribed aiming arm 10. For example, the bores 12 of the aiming arm 10 may be perfectly aligned with the center (e.g., center C1 or C2 shown in FIGS. 1A and 1B) of one of multiple hole positions of a combination hole (rather than with the central point, e.g., center C3 shown in FIGS. 1A and 1B of a combination hole). The bore 12 may receive a tool guide in only one position (rather than in two positions). Thus, it will be appreciated that a guide with a center sleeve (rather than one with an eccentric sleeve) could be used to align a tool with the portion of a combination hole that the bore is aligned with. If a surgeon wishes to penetrate or access another portion of a hole, a guide with a suitably eccentric sleeve may be used. The degree of eccentricity, it will be appreciated, would be greater in this embodiment than in the aforementioned embodiments. Thus, in one embodiment, a surgeon can access different portions of a hole, preferably an elongated or overlapping hole, by selecting the appropriate sleeve (rather than by using one sleeve and selecting the appropriate orientation). The one-sleeve system, however, is preferred.

Figure 10A:
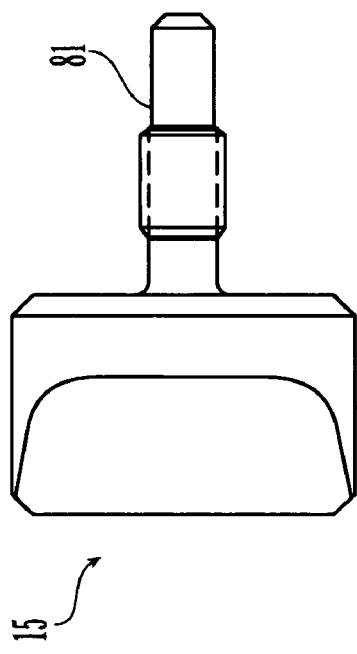
FIG. 10A is a side view of the thumb screw.
Figure 10B:
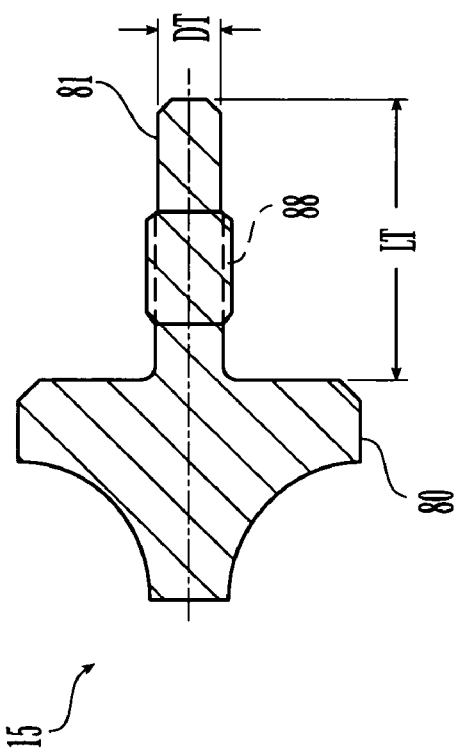
FIG. 10B is a cross-sectional view of the thumb screw of FIG. 10A.

Reference is now made to FIGS. 10A and 10B. FIG. 10A is a side view of the thumb screw 15. In this embodiment, thumb screw 15 has a head 80 and a penetrating shaft 81. Thumb screws 15 penetrate through side holes 14 of aiming arm 10 and into grooves 79 formed in the outer surface of heads 61 of lock neutral guides 60 in order to retain guides 60 in the bores 12. In a preferred embodiment, shaft 81 has external threads 88 (shown in FIG. 10B) which mate with internal threads (not shown) of side holes 14 of aiming arm 10. Shaft 81 preferably has a length LT of about 0.8 cm to about 1.2 cm and a diameter DT of about 0.19 cm to about 0.25 cm.

Figure 11:
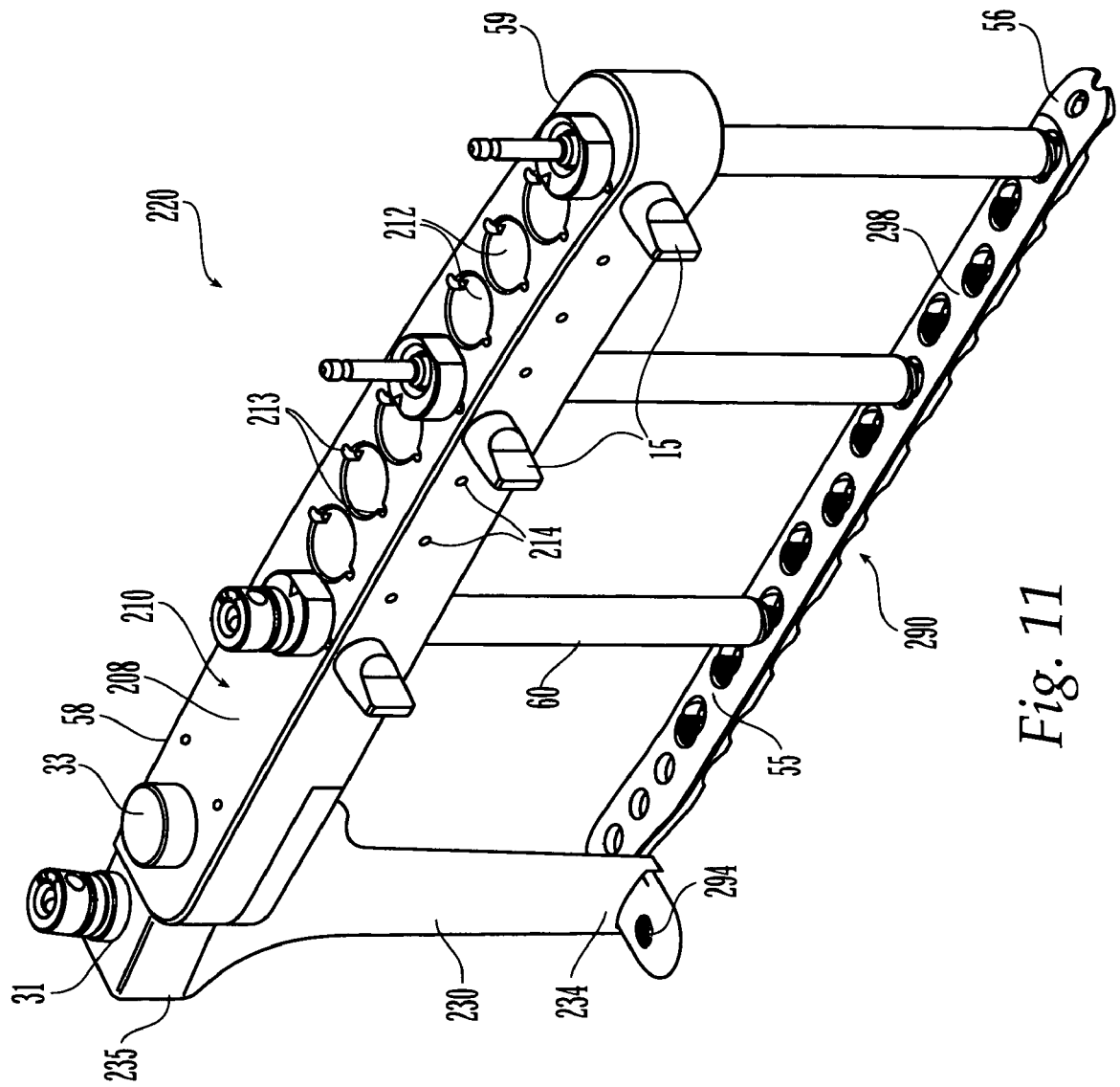
FIG. 11 is a perspective view of the assembled components of a second embodiment of the aiming guide system of the present invention.

Another embodiment, having an arm and a handle with characteristics different from those of the first embodiment, is illustrated in FIG. 11, which is a perspective view of the assembled components of an aiming guide system 220. The embodiment shown in FIG. 11 is intended for use with a bone plate which, for example, along its shaft, has a twist. The plate may be a proximal tibia plate, but could be a bone plate for other bones as well, including plates for other long bones. The plate 290 may have a head 294 and a shaft 298. The plate 290 may have holes which, due to the twist of the shaft 298, may be angled in one, two, or three planes. Moving away from the head 294, most or all of the plate holes on the shaft 298 may be oriented at progressively increasing angles (i.e., in FIG. 11 each hole may be oriented at an angle greater than the hole to its left, with the hole at the free end of the shaft 298, the end opposite the head 294, having the greatest angle as a result of the greater twist of the free end of the shaft 298).

Figure 13C:
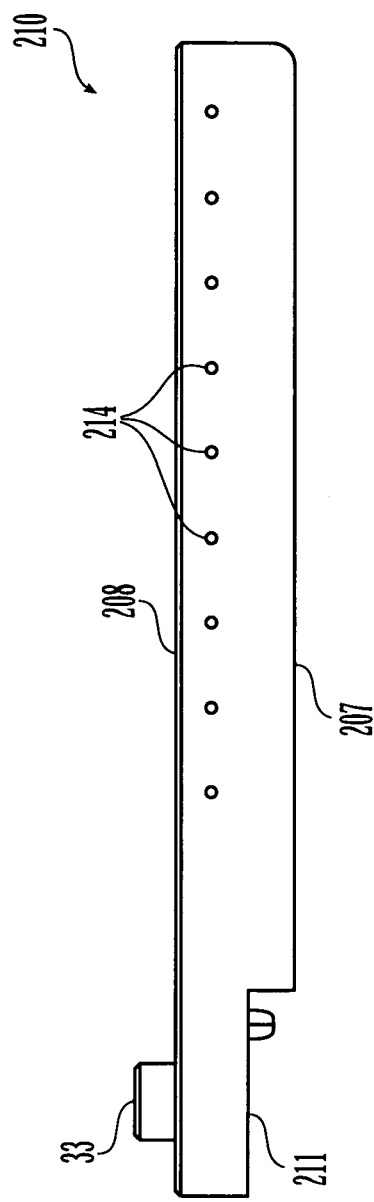
FIG. 13C is a bottom view of the aiming arm of FIG. 11.
Figure 13A:
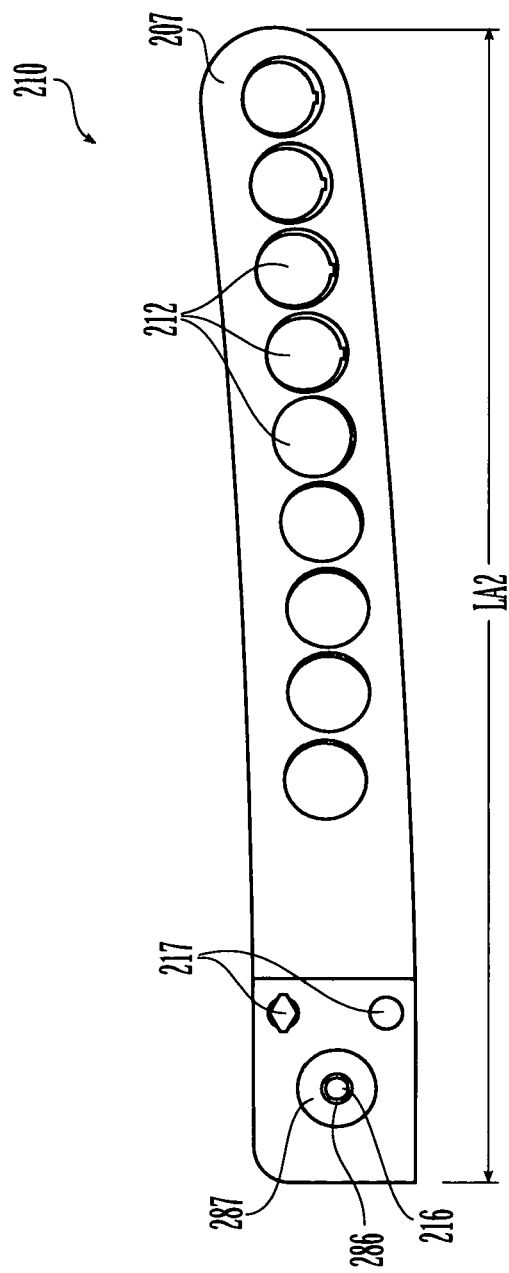
FIG. 13A is a side view of the arm of FIG. 11.
Figure 13B:
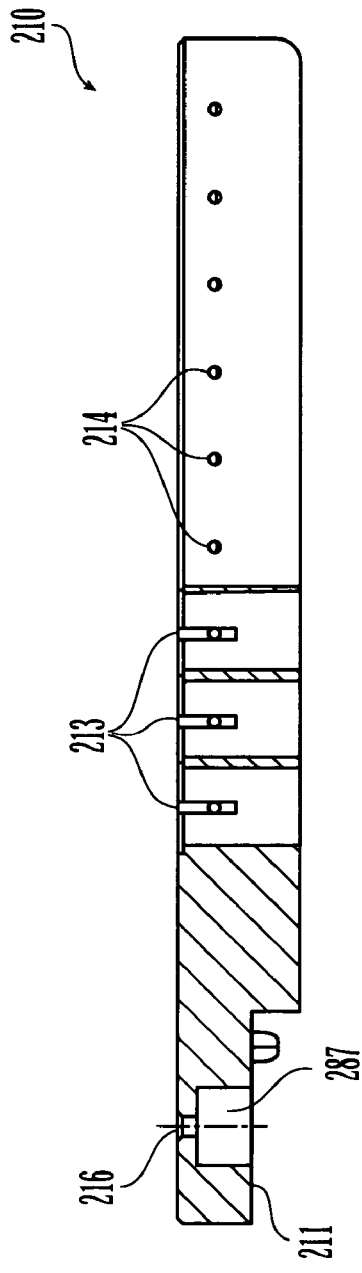
FIG. 13B is a side view, and partial cross-sectional view, of the arm of FIG. 11.
Figure 13D:
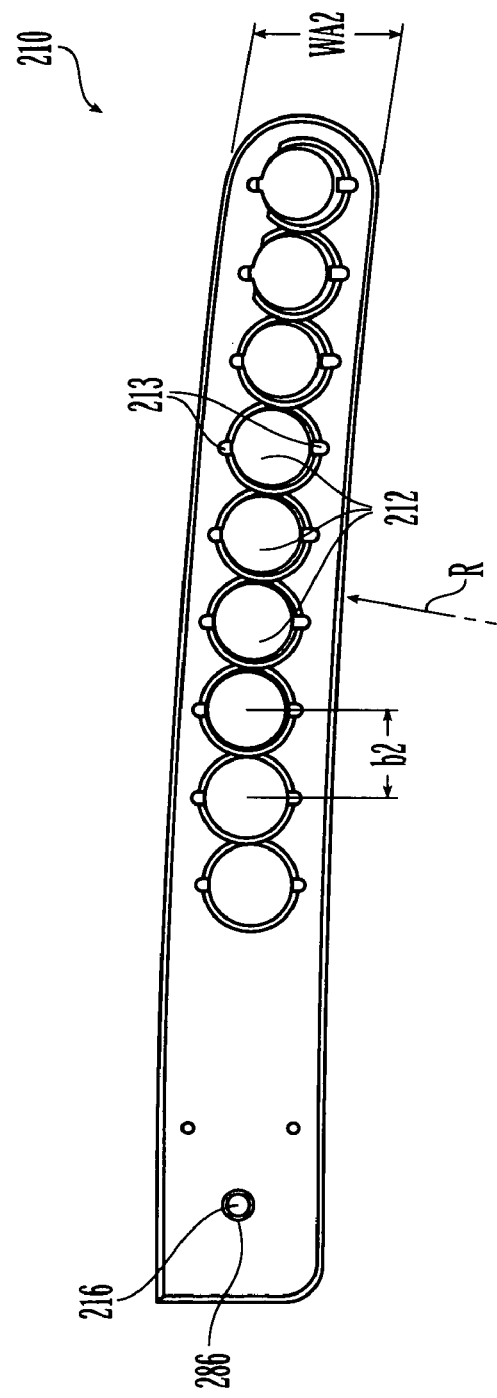
FIG. 13D is a top view of the aiming arm of FIG. 11.

Because the holes of the plate 290 are, unlike the holes of the plate 90, oriented at different angles, the aiming arm 10 may not be compatible with the plate 290 (i.e., the lock neutral guides would not be positioned at the plate holes at the proper insertion angles). The aiming arm 210, however, is specifically designed to complement a plate having a twist, a bend, or holes oriented at different angles. The aiming arm 210, unlike the aiming arm 10, may extend and be substantially non-parallel to the bone plate in a lengthwise direction. As shown in FIG. 13D (which is a top view of aiming arm 210), aiming arm 210 may be curved sideways. In one non-limiting illustrative embodiment, the radius of curvature R of arm 210 may be about 140 cm to about 170 cm. The curvature of the aiming arm 210 places the bores 212 laterally away from the plate holes. As the aiming arm 210 extends in a the general direction of the length of the bone plate 290 and away from the handle 230, most of the bores 212 are distanced progressively further away from the corresponding holes in the plate 290. The effect of locating the bores 212 away from the plate holes is to accommodate the twist in the bone plate which orients the axes of the bone plate holes at an angle relative to the top surface 208 and the bottom surface 207 of the aiming arm 210.

The arm bores 212 may be angled in a direction and at a degree dictated by and matching the angle of the corresponding hole. Thus, as the plate holes are biased from the head end 55 of the shaft 298 to the free end 56 of the shaft 298 at progressively increasing angles, so too may the bores 212 be oriented from the handle-end 58 of the arm 210 to the free end 59 of the arm 210 at progressively increasing angles. The arm bores 212 may have an angled countersink region 57 to accommodate the heads of lock neutral guides 60. Without the countersink region 57, there is only minimal contact and hence minimal stability between the heads of the lock neutral guides 60 and the aiming arm 210. Thus, the countersink region 57, which may be formed of one or more cutouts or indentations around at least a portion of the bores 212 near the upper surface 208 of the aiming arm 210, provides for additional contact between the heads of lock neutral guides 60 and the aiming arm 210.

Figure 13F:
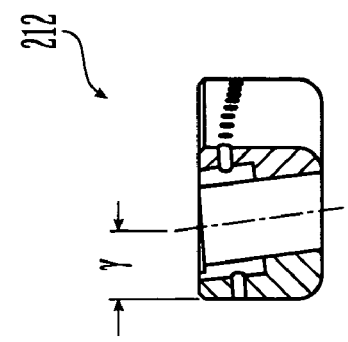
FIG. 13F is a cross-sectional view taken along axis 9A-9A of FIG. 13E.
Figure 13E:
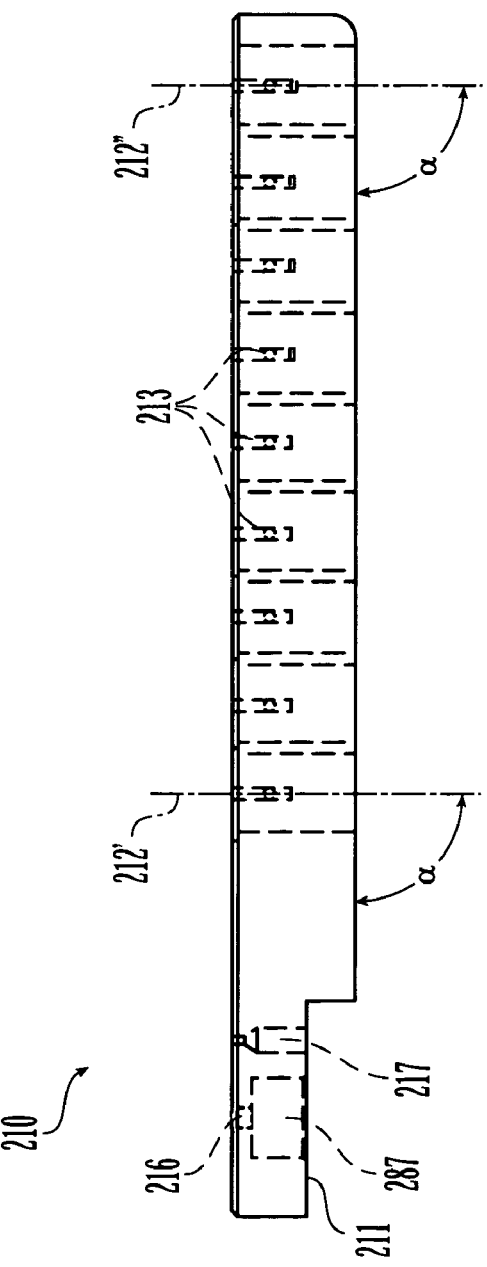
FIG. 13E is a side cross-sectional side view of the arm of FIG. 11.

In one embodiment, each of the bores 212 may be oriented at an angle relative to the aiming arm 210 in two planes. In a first plane (defined by the cross section of the arm 210 shown in FIG. 13E), the bores 212 may all be biased to the same degree, creating an angle α, as shown in FIG. 13E. In one embodiment the bores may be oriented in a direction toward the free end of the arm 210 by about 0.1° to about 1.5°, creating an angle α of about 90.1° to about 91.5°. It should be appreciated that the bores 212 can be oriented in the plane shown in FIG. 13E by a larger or smaller angle and in a different direction. It can further be appreciated that the angle of the orientation in this first plane can change for each bore 212. The bores 212 may be oriented in a second plane through the aiming arm. The bores 212 may be oriented in a direction toward the bone plate at varying degrees denoted by angle γ in FIG. 13F (which is a cross-sectional view of the arm 210 taken along the axis 9A-9A of FIG. 13E). The second plane in this illustrative embodiment is defined by the plane perpendicular to the first plane and in the plane defined by each pair of slots 213. In one embodiment, angle γ may vary from about 0° to about 5°. In one embodiment, the bore 212' (shown in FIGS. 13E and 13F) located nearest to the handle 230 may have no angle (i.e., angle γ of 0°), and the bore 212" (noted at cross section 9A-9A and shown in FIGS. 13E and 13F) located at the opposite and free end of arm 210 may have an angle γ of about 5°. The bores 212 in between the two end bores 212' and 212" may each have different angles γ between about 0° and about 5°, gradually increasing from about 0° to about 5° along the aiming arm 210 from the end bore 212' to 212". In other embodiments, the respective angles γ may be different from the aforementioned angles γ, in range, in progression/assortment, and/or in direction.

In an illustrative embodiment shown in FIGS. 13A-13F, the arm 210 has nine bores 212, and the arm 210 preferably has a length LA2 of about 21 cm to about 27 cm and a width WA2 of about 3.0 cm to about 3.6 cm. In one embodiment, each bore 212 has a diameter DB2 of about 2.0 to about 2.4 cm. In one embodiment, the distance b2 between adjacent bore 212 centers may be about 1.5 to about 2.1 cm.

In an alternative embodiment, an aiming arm having a twist and curve corresponding to the twist and curve of a bone plate, and having straight bores, may be used to accommodate a bone plate having a twist.

Reference is now made to FIGS. 12A, 12B, and 12C, which are side and top views of a handle 230 for the aiming guide system 220. As shown in FIG. 12A, the handle 230 may have a longitudinal bore or chamber 237 for insertion of an interlocking bolt, which may secure the handle 230 to the bone plate 290 in similar fashion to how the interlocking bolt 40 secures the handle 30 to the plate 90, as described above. The interlocking bolt of this embodiment may be similar in form and function to the interlocking bolt 40. The interlocking bolt of this embodiment may have similar dimensions and measurements to those of the interlocking bolt 40 or may be varied as necessary.

The connection between the arm 210 and the handle 230 will now be described. As shown in FIG. 12A, the handle may have a platform 239 on which the end portion 211 (shown in FIG. 13A) of arm 210 sits, and may have an upward projection 238, which may be received in a corresponding hole 287 (shown in FIGS. 13B and 13E) on the end portion 211 of arm 210. Further aligning the handle 230 and arm portion 210, are pins (like pins 32) which may be received by holes 236 (shown in FIG. 12C) in the handle 230 and by holes 217 (shown in FIGS. 13C and 13E) of the aiming arm 210. To secure the arm 210 to the handle 230, a coupling bolt 33 may be used. The coupling bolt 33 may have a shaft 19 which may pass through a hole 216 (shown in FIGS. 13B, 13D, and 13E) in the aiming arm 210 and mate with a hole 233 on the upper surface of the projection 238 of the handle 230. Shaft 19 of coupling bolt 33 may have external threads 85 (shown in FIG. 7) to mate with corresponding internal threads 286 (identified in FIG. 13D) of the hole 216 of aiming arm 210 and with corresponding internal threads 246 on the inner surface of hole 233 on the platform 239 of the handle 230.

Figure 12D:
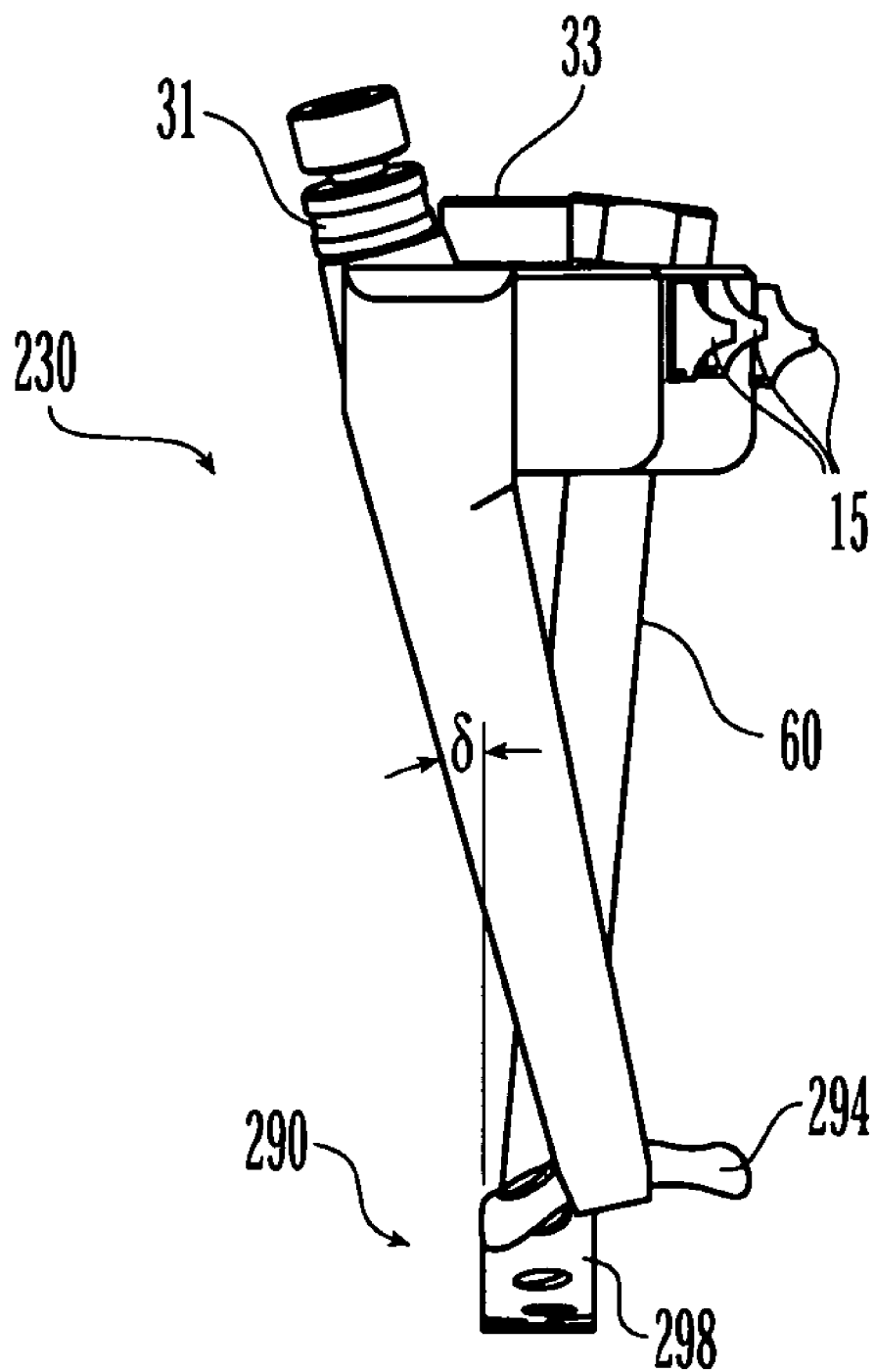
FIG. 12D is a rear view of the assembled components of the aiming guide system of FIG. 11.

In an optional embodiment, the handle 230, unlike the handle 30, may extend from the plate at a non-perpendicular angle δ with respect to the plane defined by the upper surface of the head 294 of the plate 290. The handle 230 may extend at a non-perpendicular angle, for example, in order to provide space for the use of additional instrumentation to be used to operate the system. As a non-limiting example, handle 230 may extend from the plate 290 at an angle δ from about 10° to about 20° as shown in FIG. 12D. The angle δ may be determined by the orientation of the reference hole in which the interlocking bolt is inserted. The handle 230 preferably, in a non-limiting example, has a height HH2 of about 10 cm to about 14 cm, although other dimensions are probable.

The lock neutral guides 60 may be used with aiming arm 210 as they are used with aiming arm 10. Bores 212 have diametrically opposed slots 213 on their inner surfaces. To secure the guides 60 in the bores 212, thumb screws 15 may penetrate side holes 214 of aiming arm 210 and may otherwise be used as described above in connection with the first preferred embodiment.

While the present invention has been described with reference to the preferred embodiments, those skilled in the art will recognize that numerous variations and modifications may be made without departing from the scope of the present invention. As a non-limiting illustrative example, in order to obtain the proper alignment between the guide sleeves and the desired bone plate, the bores through the aiming arm can be arranged at different angles—and in one, two, or three planes—through the aiming arm and the aiming arm can be curved, twisted, or bent in one, two, or three planes which will all be a matter of design choice. Accordingly, it should be understood that the embodiments of the invention described above are not intended as limitations on the scope of the invention, which is defined only by the following claims.

What is claimed is:

1. A device for aligning at least one surgical tool with a hole in a bone plate extending along a longitudinal axis, the device comprising:
   a handle portion including a coupling structure for coupling the handle portion to a bone plate in a desired orientation relative thereto;
   an arm portion extending along an arm portion longitudinal axis between first and second ends, the arm portion being coupleable to the handle portion in a desired orientation relative thereto, wherein, when coupled to the handle portion in the desired orientation, the arm portion longitudinal axis extends transverse to a longitudinal axis of the handle portion, the arm portion defining top and bottom surfaces and including a first bore extending through the arm portion from the top surface to the bottom surface, wherein an axis defined by the first bore is transverse to the arm portion longitudinal axis; and
   a first tool guide extending along a first tool guide longitudinal axis from the first bore of the arm portion toward a bone plate coupled to the handle portion, the first tool guide defining a first channel,
   wherein the first bore and the first tool guide are configured and adapted to permit the first tool guide to be received in the first bore in a selected one of two different preset positions, each of the selected preset positions offsets the first tool guide longitudinal axis from a center of the first bore in a different direction.

2. The device of claim 1, wherein a longitudinal axis of the first bore is offset from the arm portion longitudinal axis.

3. The device of claim 1, wherein the first bore includes two diametrically opposed slots extending along at least a portion of a length of the first bore, the first tool guide having diametrically opposed knobs extending outwardly from the first tool guide, the slots configured and dimensioned to mate with the knobs to align the first tool guide in the first bore.

4. The device of claim 3, wherein a first one of the preset positions is located 180 degrees from a second one of the preset positions.

5. The device of claim 3, wherein the first tool guide has a head and a sleeve portion, the first channel being centered with respect to the sleeve portion, and the sleeve portion being eccentric with respect to the head.

6. The device of claim 5, wherein, in a first one of the preset positions, the eccentric sleeve portion of the first tool guide and the first channel are aligned with a first portion of a hole in a bone plate and, in a second one of the preset positions, the eccentric sleeve portion and the first channel are aligned with a second portion of a hole in a bone plate.

7. The device of claim 5, wherein a central longitudinal axis of the sleeve portion of the first tool guide is offset from a central longitudinal axis of the head by a distance of approximately 0.16 cm to approximately 0.20 cm.

8. The device of claim 1, wherein the first bore is aligned with a central point of a bone plate hole.

9. The device of claim 1, wherein the first bore is aligned with a center of one portion of a bone plate hole.

10. The device of claim 1, wherein an arrangement of bores along the arm portion substantially matches arrangement of holes along at least a portion of a bone plate to be coupled to the handle.

11. The device of claim 1, wherein the first bore is oriented perpendicular to the top surface of the arm portion.

12. The device of claim 1, wherein the at least one first bore is oriented at a non-perpendicular angle with respect to the top surface of the arm portion.

13. The device of claim 12, wherein the first bore is angled in one of one, two, or three planes with respect to the top surface of the arm portion.

14. The device of claim 13, wherein the angle formed in each plane is approximately 0° to 5°.

15. The device of claim 1, wherein the first tool guide is at least one of the group comprising a drill bit, a trochar, and a bone tap.

16. The device of claim 1, wherein the handle portion has a chamber, and further comprising an interlocking bolt configured to extend though the chamber and into a hole in a bone plate to be coupled thereto.

17. The of claim 16, wherein the chamber extends the length of the handle portion.

18. The device of claim 16, wherein the interlocking bolt has a head, shaft, and end portion, the end portion having threads for engaging a hole in a bone plate.

19. The device of claim 18, wherein an internally-threaded locking nut, configured and dimensioned to mate with external threads on the interlocking bolt, is positioned between the head of the interlocking bolt and the top surface of the handle portion.

20. The device of claim 1, wherein the arm portion is aligned with the handle portion by mating pins configured and dimensioned to mate with holes in the bottom surface of the arm portion and holes in the top surface of the handle portion.

21. The device of claim 1, wherein the handle portion is secured to the arm portion by a coupling bolt.

22. The device of claim 1, further comprising a thumb screw threaded into a corresponding recess in the side of the arm portion to retain the first tool guide in the first bore.

23. The device of claim 1, wherein rotating the first tool guide from a first preset position to a second preset position moves the channel relative to the arm portion longitudinal axis.

24. The device of claim 1, wherein a first one of the preset positions corresponds to a first configuration in which a distal end of the first tool guide is in alignment with a first portion of a first combination hole of the bone plate, and a second one of the preset positions corresponds to second configuration in which the distal end of the first tool guide aligns with a second portion of the first combination hole.

25. An device for aligning at least one surgical tool with a hole in a bone plate extending along a longitudinal axis, the device comprising:
   a handle portion including a coupling structure for coupling the handle portion to a bone plate in a desired orientation relative thereto;
   an arm portion extending along an arm portion longitudinal axis between first and second ends, the arm portion being coupleable to the handle portion in a desired orientation relative thereto, wherein, when coupled to the handle portion in the desired orientation, the arm portion longitudinal axis extends transverse to a longitudinal axis of the handle portion, the arm portion defining top and bottom surfaces, and including a first bore extending through the arm portion from the top surface to the bottom surface, wherein an axis defined by the first bore is transverse to the arm portion longitudinal axis; and
   a first tool guide extending along a first tool guide longitudinal axis from the first bore of the arm portion toward a bone plate coupled to the handle portion, the first tool guide including a sleeve portion defining a channel, the tool guide having a head, the head being positioned at least partially within the first bore, the channel being centered with respect to the sleeve portion, and the sleeve portion and channel being eccentric with respect to the head, wherein the first bore and the first tool guide are configured and adapted to permit the first tool guide to be received in the first bore in a selected one of two different preset positions, each of the selected preset positions offsets the first tool guide longitudinal axis from a center of the first bore in a different direction.

26. The device of claim 25, wherein the first one bore is offset from the longitudinal axis of the arm portion.

27. The device of claim 25, wherein the first bore includes two diametrically opposed slots extending along at least a portion of a length of the first bore, the slots configured and dimensioned to mate with diametrically opposed knobs extending radially outward from the first tool guide.

28. The device of claim 27, wherein a first one of the preset positions is located 180 degrees from a second preset position.

29. The device of claim 27, wherein, in a first one of the preset positions, the eccentric sleeve portion of the first tool guide and the channel are aligned with a first portion of a hole in a bone plate coupled to the handle and, in a second one of the preset positions, the eccentric sleeve portion and channel are aligned with a second portion of a hole in a bone plate coupled to the handle.

30. The device of claim 25, wherein the first bore is aligned with a central point of a hole in a bone plate.

31. The device of claim 25, wherein the first bore is aligned with a center of one portion of a hole in a bone plate.

32. The device of claim 25, wherein an arrangement of bores along the arm portion substantially matches an arrangement of holes along at least a portion of a bone plate to be coupled to the handle.

33. The device of claim 25, wherein the first bore is oriented perpendicular to the top surface of the arm portion.

34. The device of claim 25, wherein the first bore is oriented at a non-perpendicular angle with respect to the top surface of the arm portion.

35. The device of claim 34, wherein the first bore is angled in one of one, two, or three planes with respect to the top surface of the arm portion.

36. The device of claim 35, wherein the angle formed in each plane is approximately 0° to approximately 5°.

37. The device of claim 25, wherein the handle portion is aligned with the arm portion by mating pins with holes at the bottom surface of arm portion and with corresponding holes at the top surface of the handle portion.

38. The device of claim 25, wherein the handle portion is secured to the arm portion by a coupling bolt.

39. The device of claim 25, wherein the handle portion has a chamber through its length and an interlocking bolt configured to extends through the chamber and into a hole in a bone plate to be coupled thereto.

40. The device of claim 39, wherein the interlocking bolt has a head, shaft, and end portion configured to be threaded into a hole in a bone plate to be coupled to the handle.

41. The device of claim 40, wherein the connection between the interlocking bolt and a bone plate is tightened with a locking nut positioned between the head of the interlocking bolt and the top surface of the handle portion.

42. The device of claim 25, further comprising a thumb screw threaded into a corresponding recess in the side of the arm portion to retain the tool guide in the bore.

43. The device of claim 25, wherein a central longitudinal axis of the sleeve portion is offset from a central longitudinal axis of the head a by distance of between approximately 0.16 cm and approximately 0.20 cm.

44. The device of claim 25, wherein rotating the first tool guide from a first preset position to a second preset position moves the channel relative to arm portion longitudinal axis.

* * * * *